(12) United States Patent
Keiser et al.

(10) Patent No.: US 7,917,373 B2
(45) Date of Patent: Mar. 29, 2011

(54) SYSTEM AND PROCESS FOR PRODUCING AN INDIVIDUAL FORMULATION OF PHYSICAL ENHANCER

(76) Inventors: Michael W. Keiser, Cincinnati, OH (US); Michael H. Folan, Madeira, OH (US)

( * ) Notice: Subject to any disclaimer, the term of this patent is extended or adjusted under 35 U.S.C. 154(b) by 1648 days.

(21) Appl. No.: 10/851,444

(22) Filed: May 21, 2004

(65) Prior Publication Data
US 2004/0236609 A1    Nov. 25, 2004

Related U.S. Application Data

(60) Provisional application No. 60/472,945, filed on May 23, 2003.

(51) Int. Cl.
G06Q 10/00 (2006.01)
G06F 19/00 (2006.01)
A23L 1/30 (2006.01)
(52) U.S. Cl. .................................. 705/2; 705/3; 426/311
(58) Field of Classification Search .................. 705/2–3; 707/10
See application file for complete search history.

(56) References Cited

U.S. PATENT DOCUMENTS

| | | | |
|---|---|---|---|
| 5,704,350 A * | 1/1998 | Williams, III | 600/300 |
| 5,780,094 A | 7/1998 | King | |
| 5,954,640 A | 9/1999 | Szabo | |
| 6,051,236 A | 4/2000 | Portman | |
| 6,250,609 B1 | 6/2001 | Cheng et al. | |
| 6,296,892 B1 | 10/2001 | Elseviers et al. | |
| 6,368,113 B1 | 4/2002 | Unger et al. | |
| 6,455,511 B1 | 9/2002 | Kampinga et al. | |
| 6,510,430 B1 * | 1/2003 | Oberwager et al. | 707/10 |
| 2003/0091969 A1 | 5/2003 | Supinski et al. | |
| 2003/0228999 A1 | 12/2003 | Donovan et al. | |
| 2004/0018475 A1 | 1/2004 | Healey et al. | |

OTHER PUBLICATIONS www.gatorade.com from www.archive.org, Apr. 1, 2002.*
"Effect of Beverage Osmolality on Intestinal Fluid Absorption During Exercise", C.V. Gisolfi, R.W. Summers, G.P. Lamber, and T. Xia, Journal of Applied Physiology, 85:1941-1948, 1998.*

* cited by examiner

Primary Examiner — Luke Gilligan
Assistant Examiner — Joseph Burgess
(74) Attorney, Agent, or Firm — Lafkas LLC; David M. Lafkas (57) ABSTRACT

The present invention is an interactive process and system for formulating a unique digestible physical enhancer for an individual by way of a computer system by displaying one or more statements to an individual using a client's computer, wherein the statements comprise potential formula ingredients. A server device then receives one or more responses from the client computer indicating proposed formula ingredients chosen by the individual and amounts of formula ingredients chosen by the individual. An absorption ability is determined for the proposed formula based upon proposed formula ingredients chosen by individual and amounts of formula ingredients chosen by individual. The individual has the ability to tailor the enhancer by performing the following as many times as needed. Upon receiving approval of proposed unique formula by the individual, the approved unique formula is processed by server device and the approved unique formula is produced for the individual.

21 Claims, 5 Drawing Sheets

SYSTEM AND PROCESS FOR PRODUCING AN INDIVIDUAL FORMULATION OF PHYSICAL ENHANCER

CROSS REFERENCE TO RELATED APPLICATION

The present application claims priority to U.S. patent application No. 60/472,945 filed on May 23, 2003.

BACKGROUND

1. Field of the Invention

The present invention relates generally to development of a physical enhancer for humans. Particularly, the invention relates to a unique digestible physical enhancer for consumption by a human consumed in conjunction with physical activity.

2. Discussion of the Prior Art

When it comes to improving athletic performance and reducing injuries, knowing when, what and how often to ingest particular replenishment chemicals can be key. As such, the marketplace has seen an excessive influx of sports supplements, beverages and the like over the past several years for replenishing fluids, nutrients, electrolytes and the like during exercise.

During exercise regimes of various levels of duration and intensity, individuals undergo different chemical changes based on numerous variables including, for example, the length and type of exercise program, the age and physical fitness of the individual participant, the exterior environment such as temperature and weather, and the like. Because individuals react differently based on these and other unnamed and unidentified variables, individuals lose and need to replenish and/or enhance different chemicals to his or her body.

Thus, individuals need to uniquely replenish or enhance their own body with a variety of one or more chemical ingredients typically available in the marketplace. However, depending on the individual, the number, type and form of chemicals to be replenished or enhanced during a particular exercise regime can be small or very large.

Typically, chemicals for replenishing or enhancing physical abilities during exercise regimes are available, for example, as sports beverages, powders, supplements, vitamins, gels, food bars, etc. These commercially available products are not often practical for exercise of various levels of duration and intensity, wherein the individual is not able to practically carry one or more sports beverages to provide particularly desirable replenishment or enhancement chemicals, one or more packets of powders to provide other particularly desirable replenishment or enhancement chemicals, one or more vitamin and/or mineral capsules, as well potentially carrying one or more gel packs and/or food bars.

Further to the problem of where to carry so many products on the individual, such commercially available enhancement products often contain unwanted and/or unnecessary ingredients. For example, an individual may not want any protein during his or her exercise regime, but a particular food bar that contains the protein desired by the individual may contain an unwanted protein type. In addition, consuming the generally available enhancer products means potentially ingesting, for example, undesired binders, excessive fillers, preservatives and lubricants, as well as micronutrients.

Such problems are not limited to athletes. For example, individuals in rehabilitation, patients in nursing care facilities, individuals on high protein diets, and the like may be looking to increase particular enhancement ingredients, but not with the combination of unwanted chemicals.

Moreover, particular generally available enhancement products may often be difficult to locate for purchase, be hard to swallow and may contain some vitamins or minerals that are not needed or may not have enough of what enhancement chemicals are needed or desired.

Further, an individual may desire particular types and/or forms or particular physical replenishers and enhancers such as protein. There is a vast combination of ingredients commercially available to individuals in a large number of different products. However, the commercially available products may not offer just one of the desired types of particular ingredients, and/or may not describe the origin of a particularly desired ingredient.

For the above reasons, an individual may surrender their personal replenishment and/or enhancement program or never have the opportunity to improve and achieve the physical activity goals they had set for themselves.

Individuals learn what chemicals benefit their bodies by research and careful observations of their bodies during physical activities in conjunction with research into the latest studies and available enhancement chemicals. One of the primary areas for such research is the Internet. The Internet is an international network of interconnected computers that enables many multiples of people to communicate with one another in "cyberspace" and to access vast amounts of information from around the world. This network of networks uses certain standard procedures for regulating data transmission between computers such as Transmission Control Protocol/Internet Protocol (TCP/IP) or HyperText Transfer Protocol (HTTP) for HyperText Markup Language (HTML) documents. The physical connections of the Internet and the protocols and communication procedures of the Internet are well-known to those in the art.

Through the Internet, individuals may seek out health and nutrition information to educate themselves about replenishing and enhancing their bodies during exercise regimes and use this detailed information to make informed purchase decisions. However, even with the availability of this information through the Internet, it is very difficult for an individual to navigate through the myriad of available information to find and/or purchase enhancement products comprising enhancement chemicals that the individual needs and/or desires without the presence of extraneous chemicals in the purchased and consumed product.

Individuals can also obtain opinions regarding replenishing and enhancing their exercise regimes from expert nutritionists or pharmacists' services. Based on communications between the individual and nutritionist and/or pharmacist, the individual may be presented with a unique set of replenishers and/or enhancers that are recommended to be ingested during different stages of the exercise regime. However, despite the expertise of the nutritionist and/or pharmacist, the individual is still not provided with a unique formula that is easily carried during the exercise regime, readily commercially available, and does not contain unwanted ingredients. The expertise provides the individual merely with a list of ingredients that the individual is recommended to ingest.

The Internet is changing every area of humanity, primarily through the use of host computers, those computers that store information and relay communications. Individuals can obtain access to the Internet from many different sources, generally hosts themselves or entities with a host affiliation. Many corporations provide their employees with access through an office network; most colleges and universities provide access for their students and faculty; many communities and local libraries provide free access; and an increasing number of storefront computer coffee shops provide access for a small hourly fee. Several major national Internet online services such as AMERICA ONLINE®, COMPUSERVE®, the MICROSOFT NETWORK® and PRODIGY® offer access to their own extensive proprietary networks, as well as a link to the much larger resources of the Internet.

Anyone with access to the Internet may take advantage of a wide variety of communication and information retrieval methods. These methods are constantly evolving. Methods such as electronic mail (hereinafter "e-mail"), automatic mailing list services (hereinafter "mail exploders" and/or "listservs"), "newsgroups," "chat rooms," and the "World Wide Web (hereinafter "Web"), can be used to transmit text; most can transmit sound, pictures, and moving video images. Taken together, these tools constitute a unique medium known to its users as "cyberspace" located in no particular geographical location but available to anyone, anywhere in the world, with access to the Internet.

The best known category of communication over the Internet is the Web, which allows users to search for and retrieve information stored in remote computers, as well as, in some cases, to communicate back to designated sites. In practical terms, the Web comprises numerous documents stored in different computers all over the world. Some of these documents are simply files containing information, while others are more extensive documents known as "Web pages." Each such document and Web page has its own unique address like a telephone number. Web pages typically contain information and sometimes allow the viewer to communicate with the page's (or "site's") author. The Web pages generally also contain "links" to other documents created by that site's author or to other (generally) related sites.

To navigate the Web, an individual may either type the address of a known page or enter one or more keywords into a commercial "search engine" in an effort to locate sites on a subject of interest. A particular Web page may contain the information sought by the individual or, through its links, it may be an avenue to other documents located anywhere on the Internet. Some Web pages provide information whereas other Web pages offer goods or services for purchase by credit card through online communication. Access to most Web pages is freely available, but some allow access only to those who have purchased the right from a commercial provider. The Web is thus comparable, from the individual's viewpoint, to both a vast library including millions of readily available and indexed publications and a sprawling mall offering goods and services.

As noted, the power of the Internet goes far beyond delivering consumer information. From the sales of goods and services point of view, the Web constitutes a vast platform from which to market and sell to a worldwide audience of millions of buyers. Users of the Internet may purchase goods or services, register their opinion on a variety of topics through online surveys, or manipulate game pieces in playing games against opponents thousands of miles away. All of these interactive actions may be performed from the comfort of the user's own home.

SUMMARY

The present invention describes an interactive process for formulating a unique digestible physical enhancer for an individual by way of a computer system comprising displaying one or more statements to the individual using a client's computer, wherein the statements comprise potential formula ingredients and receiving one or more responses at a server device from the client computer indicating proposed formula ingredients chosen by the individual and amounts of formula ingredients chosen by the individual. An absorption ability is determined of a proposed formula based upon proposed formula ingredients chosen by individual and amounts of formula ingredients chosen by the individual. Approval is received and processed to produce the approved unique formula for the individual.

The present invention of various exemplary embodiments further describes an interactive process for formulating a unique digestible physical enhancer for an individual by way of a computer system comprising displaying one or more statements to the individual using a client's computer, wherein the statements comprise potential formula ingredients. A server device receives one or more responses from the client computer indicating proposed formula ingredients chosen by the individual and amounts of formula ingredients chosen by the individual. An absorption ability is determined of a proposed formula based upon proposed formula ingredients chosen by individual and amounts of formula ingredients chosen by the individual. The individual can tailor the proposed formula ingredients and amounts of ingredients as many times as needed. Upon modifying the proposed unique formula, the absorption ability is re-determined. Approval is received and processed to produce the approved unique formula for the individual.

Also described is a system for formulating a unique digestible physical enhancer for an individual comprising a client computer, wherein the client computer displays one or more statements to the individual such that the one or more statements comprise potential formula ingredients, and a server device. The server device receives one or more responses from the client computer indicating proposed formula ingredients chosen by the individual and amounts chosen by the individual, determines an absorption ability based upon the proposed formula ingredients chosen by the individual and amounts chosen by the individual, forwards proposed unique formula ingredients and amounts chosen by the individual to the individual, receives one or more modifications to the proposed unique formula ingredients and amounts from the individual, re-determines the absorption ability based upon the one more modifications made by the individual, receives approval of proposed unique formula from the individual, processes approved unique formula, and forwards processed approved unique formula to be produced for the individual.

BRIEF DESCRIPTION OF THE DRAWINGS

Various exemplary embodiments of the present invention, which will become more apparent as the description proceeds, are described in the following detailed description in conjunction with the accompanying drawings, in which.

DETAILED DESCRIPTION

In exemplary embodiments of the present invention, an individual connects to a server through a computer network, for example, TCP/IP over PPP dial-up lines through the Internet, Ethernet, ISDN, Frame Relay, or other known means of connecting an individual's computer to a server computer.

Figure 1:
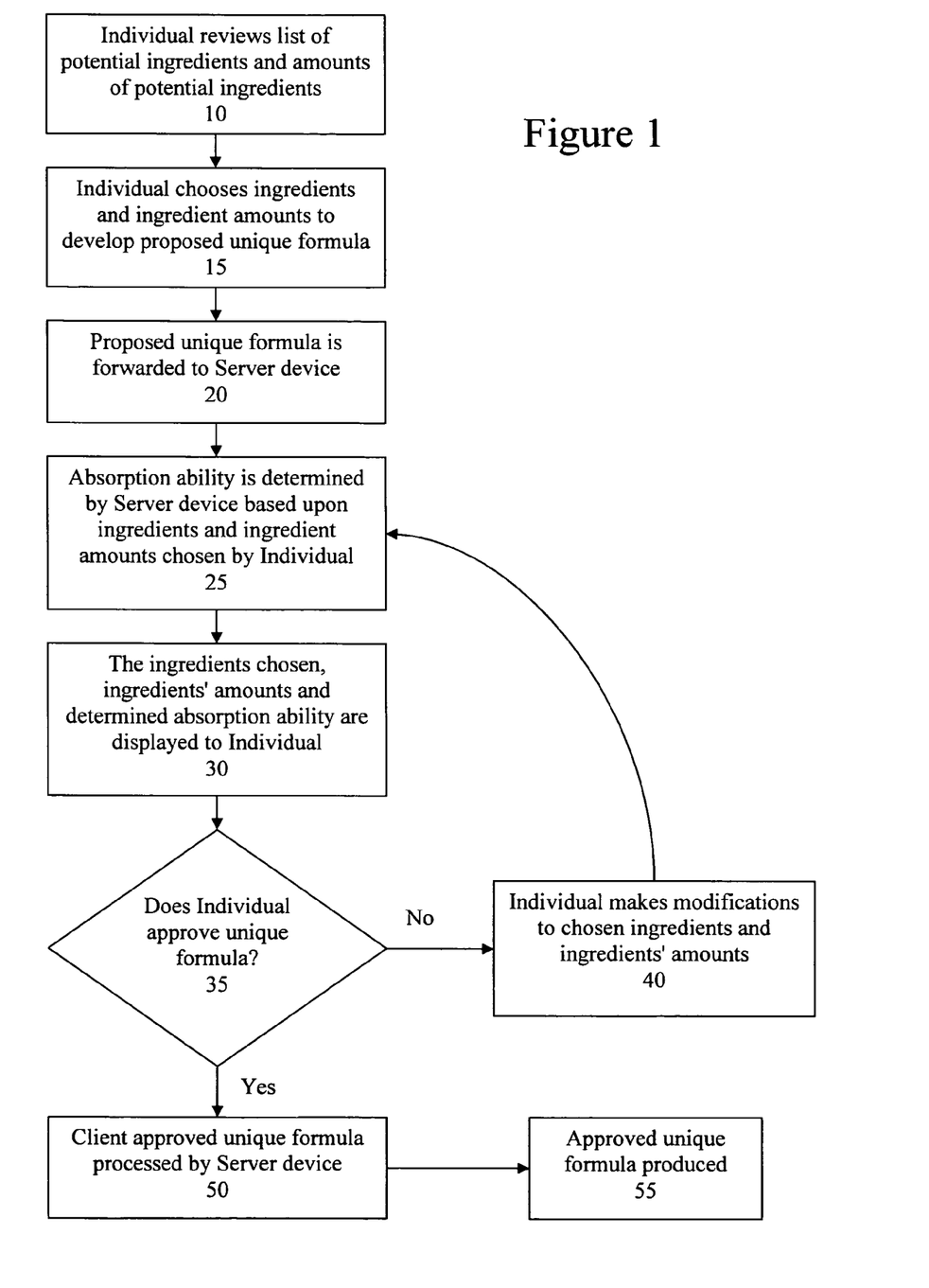
FIG. 1 is a flow diagram of an exemplary embodiment of the system process of the present invention.

FIG. 1 illustrates a flow chart of an exemplary embodiment of the present invention upon a computer interface between an individual and server to design a unique exercise regime formula. The individual reviews ingredients available through the server as represented by block 10. The ingredients available may generally include, but are not limited to, for example, flavorings, caffeine, proteins, magnesium, phosphates, antioxidants, carbohydrates, electrolytes, and creatine.

In exemplary embodiments, flavorings and/or sweeteners include, for example, commercially available flavorings and sweeteners. The flavorings and/or sweeteners may have a consistency of being, for example, granular, fine or powdered.

Carbohydrates are the fuel from which body cells obtain energy for cellular activities and the major portion of carbohydrates utilized by the body are for the breakdown of adenosine triphosphate, i.e., energy-rich phosphate bonds. Carbohydrate feeding during exercise regimes can delay fatigue for as much as sixty minutes in some individuals. A non-exhaustive list of examples of carbohydrates in various exemplary embodiments of the present invention includes glucose, maltodextrin, and a sucrose/dextrose blend.

Examples of proteins of various exemplary embodiments of the ingredients include, but are not limited to, for example, egg protein, soy protein and whey protein.

In a preferred embodiment, wherein amino acids are an ingredient, the amino acids comprise a blend of amino acids including, but not limited to, L-glutamine, L-isoleucine, L-leucine and L-valine.

Oxidative damage to cells is thought to be a causative factor in disease and aging. The culprits of such damage are free radicals or reactive species of oxygen, nitrogen or chlorine. Superoxide, hydroxyl ions, hydrogen peroxide, and nitric oxide are examples of free radicals, that is, atoms or molecules with an unpaired electron. Free radicals are naturally occurring and an important part of biological functions such as immunity, inflammation, growth and repair. However, free radicals can have negative effects when they damage proteins, lipids and nucleic acids. Free radicals are normally held in balance in biological systems by antioxidant defense mechanisms.

Oxidative stress occurs when there are more free radicals than can be dealt with due to environmental insult, disease or malnutrition. Exercise, because of an increase in oxygen demand and utilization, typically increases the formation of free radicals. An improper balance between formation and destruction of free radicals may play a role in degenerative disease and aging. As such, antioxidants added to one's body may prevent disease and deficiencies associated with free radicals, Examples of antioxidants in various exemplary embodiments of the present invention include, but are not limited to, for example, vitamin C, vitamin E and beta-carotene.

In a preferred exemplary embodiment, the antioxidants comprise a blend of antioxidants including, but not limited to, vitamin C, vitamin E and beta-carotene.

Electrolytes of various exemplary embodiments of the present invention include, but are not limited to, sodium, potassium, magnesium and calcium. Suitable sources of the electrolytes include, but are not limited to, sodium chloride, potassium phosphate, potassium citrate, and magnesium succinate. Electrolytes are optional, as with all ingredients in the exemplary embodiments of the present invention. Thus, the amount of electrolytes added is preferably suitable to affect an increase in fluid intake without resulting in an unpalatable drink.

In a preferred exemplary embodiment, the electrolytes comprise a blend of electrolytes including, but not limited to, sodium, potassium, magnesium and calcium.

In addition, a unique formula created from ingredients chosen by the individual may also contain other various nutrients. These include, but are not limited to, for example, vitamins, and minerals. Suitable vitamins may include, but are not limited to, for example, B vitamins, pantothenic acid, thiamin, niacin, niacinamide, riboflavin, iron and biotin. Minerals may include, but are not limited to, for example, chromium, magnesium and zinc.

Other ingredients including, for example, coloring and preservatives may also be added. Suitable amounts and types of all ingredients described herein vary as preferred by the individual.

In an exemplary embodiment as represented by 15 of FIG. 1, the individual identifies particular ingredients from the list of available ingredients from the server that the individual wants to include in his unique exercise regime formula. The individual also indicates the amount of each identified particular ingredient. In a preferred embodiment, the amount of each identified particular ingredient is based on a mass or weight of the identified particular ingredient. In another preferred embodiment, the amount of each identified particular ingredient is based on a relative weight of the total formula, i.e., a percentage of the whole formula.

In exemplary embodiments of the present invention, the server device displays recommended ingredients to an individual based upon, for example, the age of the individual and/or the activity, i.e., exercise regime, to be undertaken by the individual. The server device hereinafter includes a server computer and/or server program. The recommended ingredients may be an interactive communication between the server device and the individual as, for example, questions to the individual and statements to the server device input by the individual. The recommended ingredients may also be in the form of statements presented through the server device to the individual based upon variables such as, for example, age of the individual, activity of the individual, and the like.

In exemplary embodiments of the present invention, the recommended ingredients may be viewed by the individual at any point in the process of developing a proposed or modified unique formula.

Upon identification of the ingredients wanted by the individual, the ingredients chosen by the individual and amounts of each ingredient chosen by the individual are in exemplary embodiments forwarded to the server as a proposed unique formula. See block 20.

The server in the exemplary embodiment represented by block 25 analyzes the ingredients and ingredient amounts chosen by the individual and determines an absorption ability of the proposed unique formula designed by the individual.

"Absorption ability" hereinafter refers to the power and/or capacity of the individual to readily digest and assimilate the ingredients in a unique formula. The absorption ability in the exemplary embodiments of the present invention is determined based upon, for example, the osmolality, carbohydrate concentration and solubility of the ingredients of the unique formula. In various embodiments, the absorption ability is determined preferably based upon osmolality.

Osmolality is the measurement of particles in a liquid solution. Unlike molarity or molality measurements, osmolality is not affected by the weight of particles in a solution. Osmolality is the total number of solute particles per mass of solvent.

The average osmolality of human blood is about 250 to about 300. Many commercially available rehydration beverages may have an osmolality much greater than about 250 to about 300. Having an osmolality much greater than about 250 to about 325 can be problematic for the human body during an exercise regime because fluids with an osmolality much greater than that of the individual's blood is difficult for the body to quickly absorb. Thus, if the osmolality of a fluid is much more than that of the individual's blood, the fluid ingested likely will not be properly absorbed and the body will fatigue due to a lack of rehydration and non-introduction of lost chemicals.

Further, it should be noted that ingesting fluids with an osmolality much greater than that of the individual's blood can lead to physical ailments including, for example, cramping, diarrhea, and/or vomiting. Such physical symptoms arise as the intestines introduce additional fluids to mix with the ingested fluid having an osmolality greater than that of blood. The additional fluids are introduced by the body in order to decrease the osmolality of the ingested fluid and thus be able to be absorbed more readily by the body. However, if too much fluid is introduced by the digestive system to decrease the osmolality of the ingested fluid, cramping, diarrhea and/or vomiting can result.

Thus, in exemplary embodiments of the present invention, it is desired that the unique formula chosen by the individual have an absorption ability determined based upon osmolality less than or equal to that of the blood of the individual.

The absorption ability determined by the server based on the chosen ingredients and ingredients amounts by the individual in various exemplary embodiments of the present invention may be presented to the individual, preferably by way of the computer network through which the individual chose the ingredients and ingredient amounts. The determined absorption ability of exemplary embodiments may be displayed as, for example, a calculated numeric value, as a numeric or relative value on a scale, or as a symbol or symbolic message indicating whether a formula developed with the chosen ingredients and ingredient amounts would be of an acceptable value or a of a value greater than recommended.

Figure 2:
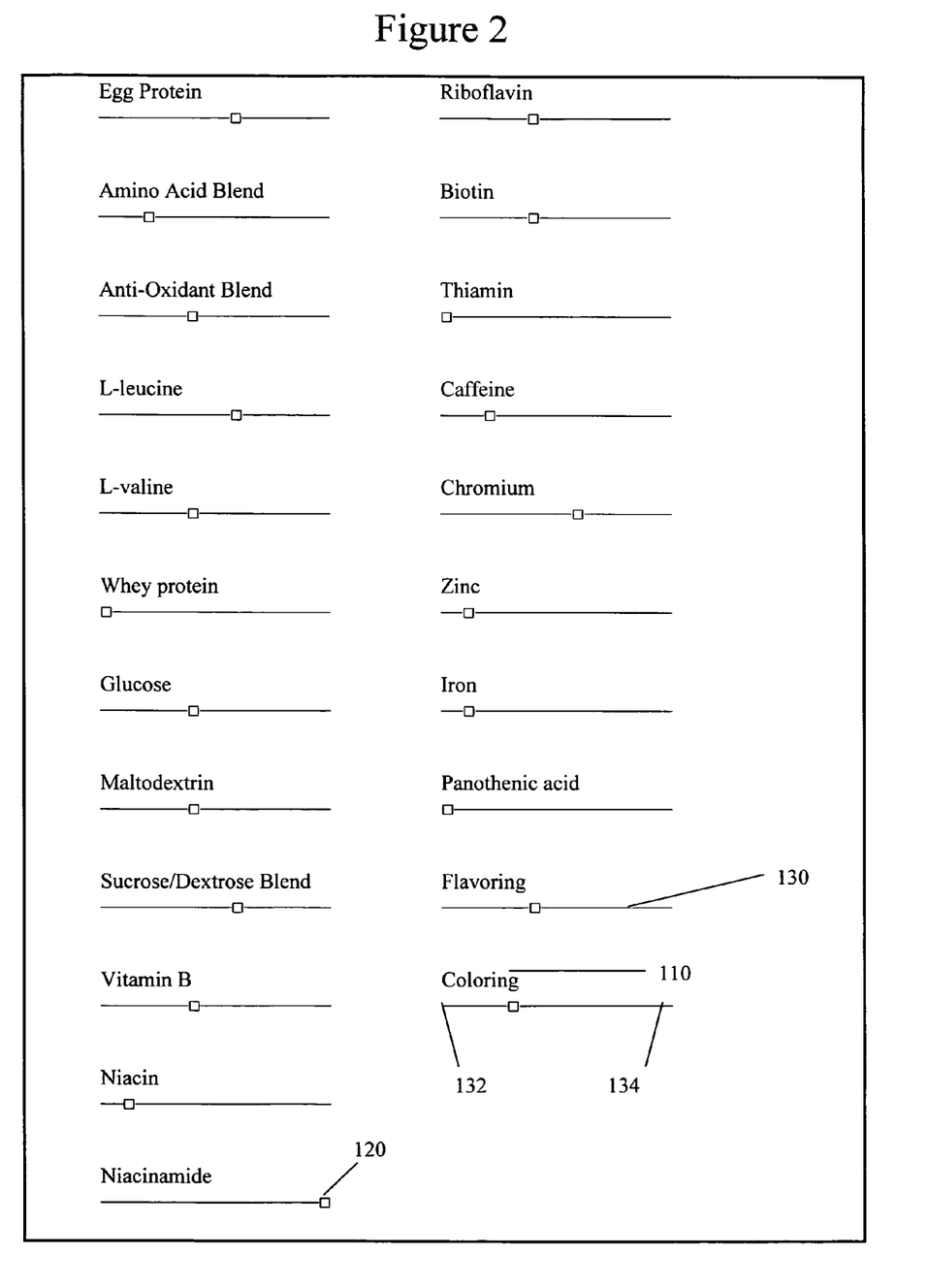
FIG. 2 is an example of an ingredient list displayable to an individual using a computer according to a various exemplary embodiments of the present invention.

FIG. 2 shows an example of a list of ingredients that can be manipulated by an individual in designing a unique formula according to the exemplary embodiments of the present invention.

Under each ingredient 110 in FIG. 2 is a sliding scale 130, wherein 132 is a smaller value and 134 is a greater value on the scale. An amount of a particular ingredient 110 is represented by 120. The amount 120 can move moved to the smaller value 132 and/or to the greater value 134 based upon the needs and desires of the individual. In a preferred embodiment, if the amount 120 is moved all the way to the smaller value 132 on the sliding scale 130, the amount of the particular ingredient 110 in the unique formula is zero. Thus, if the amount 120 is all the way to the smaller value 132, no amount of that ingredient is to be introduced to the unique formula.

In various exemplary embodiments, as the amount 120 of a particular ingredient 110 is manipulated, that is, for example, the amount 120 is moved on the sliding scale 130, the absorption ability of the unique formula being designed is determined. In various embodiments, as the absorption ability is determined, the amount of another ingredient may be changed automatically by the server to keep the determined absorption ability greater than or equal to a pre-determined value. In various embodiments, a warning may be provided to the individual if the absorption ability is equal to or greater than a pre-determined value. Such a warning may be in the form of a text message, a "pop-up window" message, a symbol, and/or an audible message.

In various exemplary embodiments, upon review by the individual of the ingredients chosen, amounts of ingredients chosen, and determined absorption ability of the proposed unique formula, the individual has the ability to approve or disapprove the proposed unique formula. See FIG. 1, block 35.

Should the individual not approve the proposed unique formula of various exemplary embodiments of the present invention, the individual may modify the proposed unique formula by, for example, canceling one or more ingredients previously chosen, adding one or more ingredients not previously chosen, decreasing the amount of one or more ingredients previous chosen, or increasing the amount of one or more ingredients previously chosen.

If the individual modifies the proposed unique formula as shown in block 40, in various exemplary embodiments of the present invention, the modified unique formula is forwarded to the server to determine the absorption ability of the modified unique formula. See block 30.

The individual has the ability to modify the ingredients chosen and ingredient amounts one or more times in various exemplary embodiments of the present invention. Upon modification of the ingredients chosen and ingredient amounts, the absorption ability will be determined and allow the individual to further modify the ingredients chosen and/or the ingredient amounts or to accept the ingredients chosen and ingredient amounts.

When the individual approves the ingredients chosen and ingredient amounts in various exemplary embodiments of the invention, a unique formula approved by the individual is processed by the server device. See block 50.

Once the formula is processed by the server, the unique formula in various exemplary embodiments is produced for the individual. See block 55.

Figure 4:
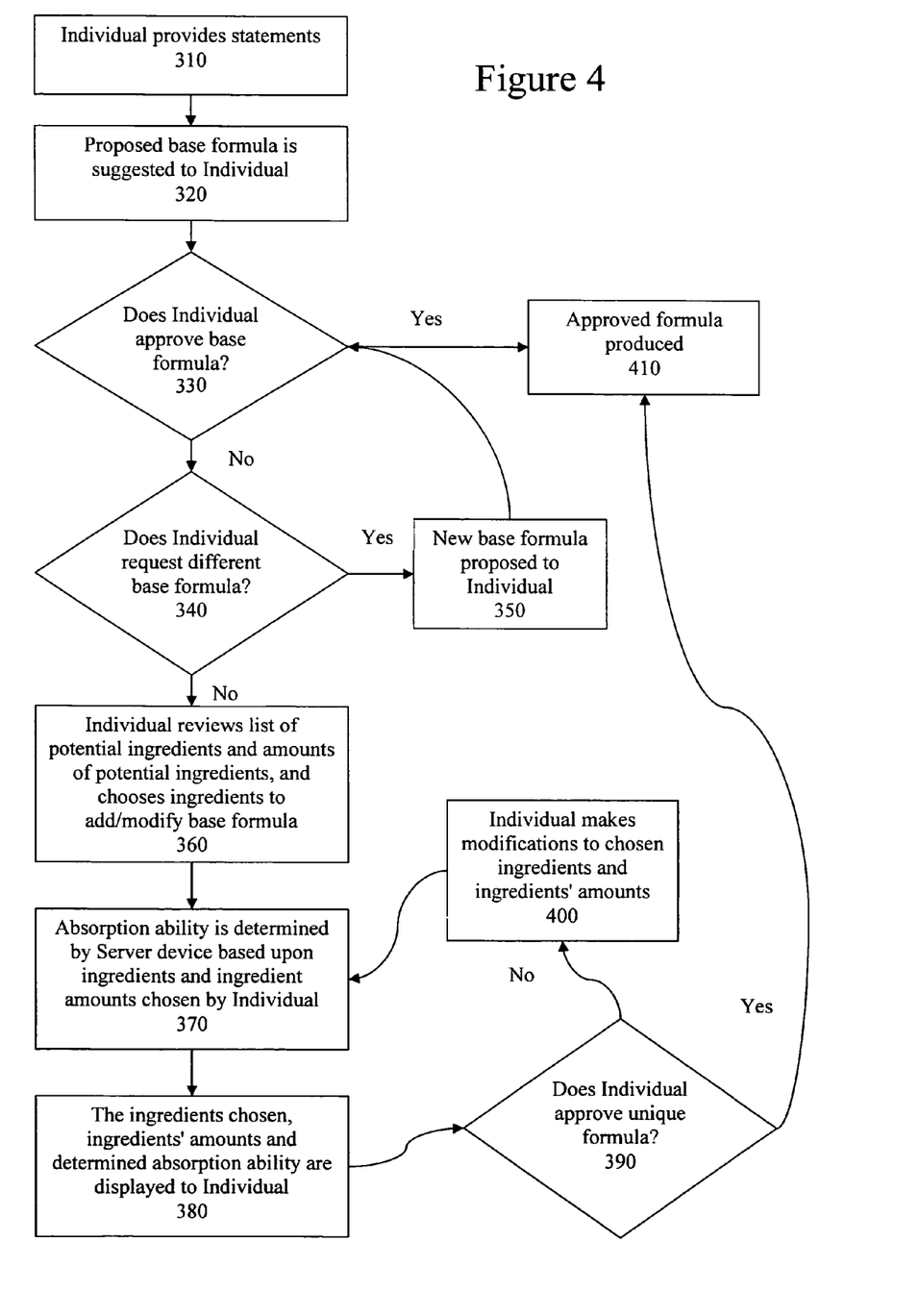
FIG. 4 is a flow diagram of another exemplary embodiment of the system process of the present invention.

Another exemplary embodiment of the present method is represented in FIG. 4. In this exemplary example, an individual provides one or more statements to the server device. See block 310. The one or more statements may include, for example, name, address, age, gender, height, weight, body mass index, type of physical activity usually performed, amount of time spent training, etc.

Based on the one or more statements provided by the individual, the server device proposes a base formula to the individual. Block 320. The proposed base formula comprises ingredients blended together to provide at least the basic physical benefits to be achieved based on the statements and to replace and enhance the chemicals lost to the body during the particular physical activity to be undertaken.

In a preferred embodiment, the proposed base formula provided to the individual is one of several predetermined formulae. In a most preferred embodiment, the server device provides one of four predetermined formulae, each of which is chosen by the server device based on the statements provided.

In block 330, the individual chooses to approve/accept the base formula provided by the server device. If the individual approves the base formula, the formula is produced. See block 410. If the individual does not approve the base formula as is and chooses to have a different base formula, block 340, the server device reexamines the statements and proposes a new base formula, block 350.

If the individual does not approve the base formula as is as the final unique formula, the individual can modify the base formula by reviewing a list of potential ingredients and amount of potential ingredients. See block 360. The individual can modify any of a number of ingredients and amounts thereof based on what the individual thinks necessary based on his experience, preferences, goals, recommendations provided by the server device, testimonials, and the like.

FIG. 2 shows an example of a list of ingredients that can be manipulated by an individual in designing a unique formula according to the exemplary embodiments of the present invention.

Upon modifying any ingredients and amounts of ingredients, the absorption ability of the modified base formula is determined, block 370, and presented to the individual. See block 380.

The individual has the ability to modify the ingredients chosen and ingredient amounts one or more times in various exemplary embodiments of the present invention. Upon modification of the ingredients chosen and ingredient amounts, the absorption ability will be determined and allow the individual to further modify the ingredients chosen and/or the ingredient amounts or to accept the ingredients chosen and ingredient amounts. See blocks 390 and 400.

Upon modification of the ingredients and ingredient amounts to the satisfaction of the individual, the individual approves the unique formula and the formula is produced. See block 410.

Figure 5:
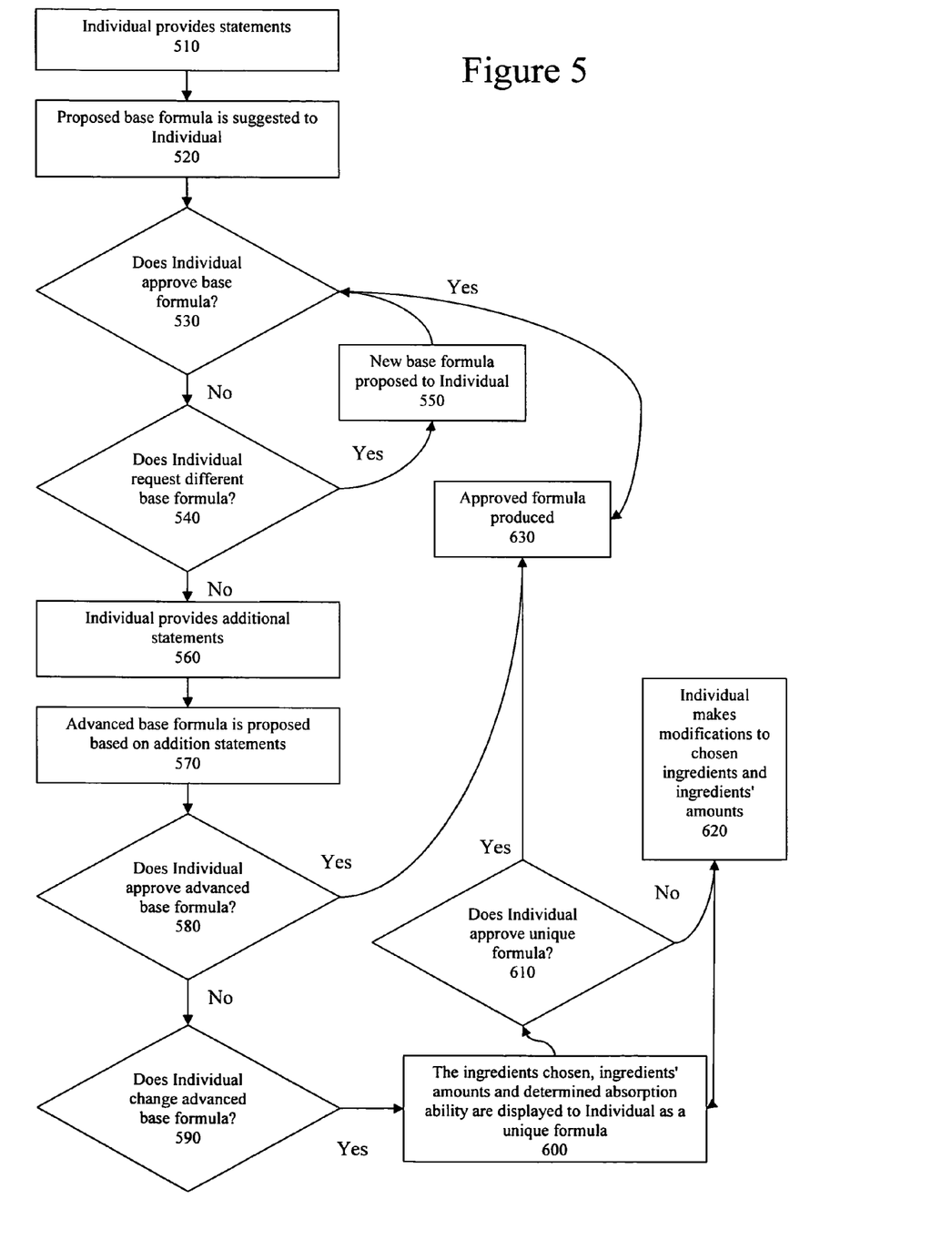
FIG. 5 is a flow diagram of a further exemplary embodiment of the system process of the present invention.

FIG. 5 represents another exemplary embodiment of the present invention. In this exemplary example, an individual provides one or more statements to the server device. See block 510. The one or more statements may include, for example, name, address, age, gender, height, weight, body mass index, type of physical activity usually performed, amount of time spent training, etc.

Based on the one or more statements provided by the individual, the server device proposes a base formula to the individual. Block 520. The proposed base formula comprises ingredients blended together to provide at least the basic physical benefits to be achieved based on the statements and to replace and enhance the chemicals lost to the body during the particular physical activity to be undertaken.

In a preferred embodiment, the proposed base formula provided to the individual is one of several predetermined formulae. In a most preferred embodiment, the server device provides one of four predetermined formulae, each of which is chosen by the server device based on the statements provided.

In block 530, the individual chooses to approve/accept the base formula provided by the server device. If the individual approves the base formula as is, the formula is produced. See block 630. If the individual does not approve the base formula as is and chooses to have a different base formula, block 540, the server device re-examines the statements and proposes a new base formula, block 550.

In this exemplary embodiment, the individual provides additional statements after the base formula is chosen. See block 560. The addition statements may relate to advanced subjects regarding, for example, the caloric needs, the fluid needs and electrolytic needs of the individual. In a preferred embodiment, the statements provided by the individual to the advanced subjects are determined, for example, on a caloric needs estimation and/or calculation based upon lean body mass determination, on sweat rate tests, sweat composition determinations, and the like.

The server device proposes an advanced base formula accounting for the advanced statements provided by the individual. See block 570. If the individual approves the advanced formula as is, the formula is produced. See blocks 580 and 630.

If the individual does not approve the advanced base formula as is, but determines that modifications are to be made to the advanced formula, the individual can modify the base formula by reviewing a list of potential ingredients and amount of potential ingredients. See blocks 580, 590 and 600. The individual can modify any of a number of ingredients and amounts thereof based on what the individual thinks necessary based on his experience, preferences, goals, recommendations provided by the server device, testimonials, and the like.

FIG. 2 shows an example of a list of ingredients that can be manipulated by an individual in designing a unique formula according to the exemplary embodiments of the present invention.

Upon modifying any ingredients and amounts of ingredients, the absorption ability of the modified base formula is determined, block 600, and presented to the individual.

The individual has the ability to modify the ingredients chosen and ingredient amounts one or more times in various exemplary embodiments of the present invention. Upon modification of the ingredients chosen and ingredient amounts, the absorption ability will be determined and allow the individual to further modify the ingredients chosen and/or the ingredient amounts or to accept the ingredients chosen and ingredient amounts. See blocks 610 and 620.

Upon modification of the ingredients and ingredient amounts to the satisfaction of the individual, the individual approves the unique formula and the formula is produced. See block 630.

In each of the exemplary embodiments, the server device further provides directions to the user for mixing and ingesting the produced formula. The directions may comprise the amount to be ingested, how often a particular amount should be ingested, based on the activity being undertaken, and the like.

Figure 3:
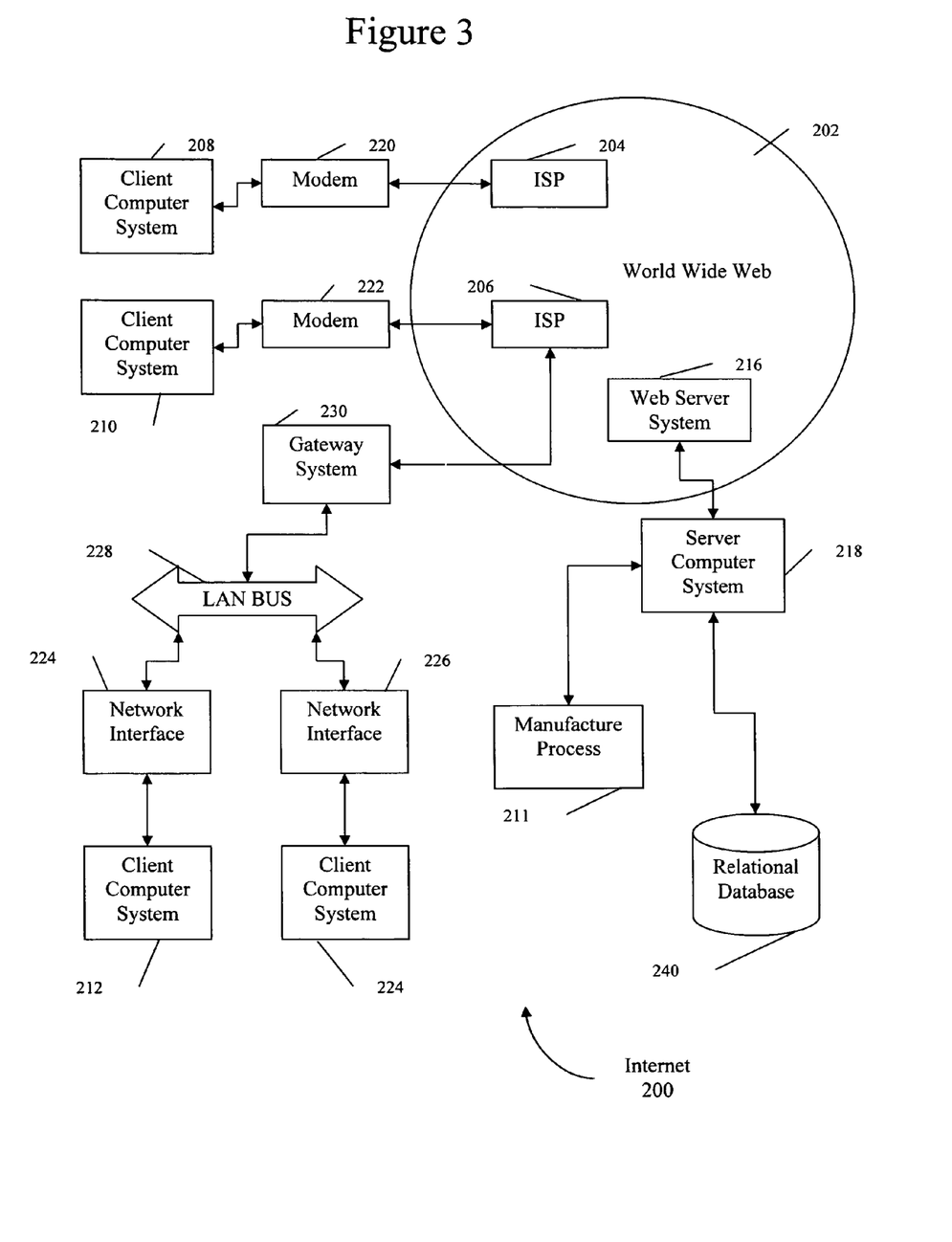
FIG. 3 is a schematic representation of the Internet with several client computer systems and a server computer system coupled to the World Wide Web according to a various exemplary embodiments of the present invention.

FIG. 3 shows Internet 200 with several client computer systems 208, 210, 212, and 214 and server computer system 218 coupled to World Wide Web 202 according to various exemplary embodiments of the present invention. Individuals' access to the World Wide Web 202 is typically provided by Internet Service Providers (ISP), such as ISP 204 and ISP 206. Individuals on client computer systems, such as clients 208, 210, 212, and 214, may be unrestricted public members and may obtain access to World Wide Web 202 through Internet Service Providers, such as ISP 204 and ISP 206. Access to World Wide Web 202 allows individuals to receive, view, and interact with Web pages. These Web pages are often provided by Web server systems, such as Web server system 216. Web server system 216 may be considered to be "on" World Wide Web 202. Often, these Web server systems are provided by the ISPs, such as ISP 204, although a computer system may be set up and connected to World Wide Web 202 as part of Internet 200 without that computer system being also an ISP. This is well-known in the art.

Web server system 216 is typically at least one computer system that operates as a server computer system ("server") and is configured to operate with the protocols of World Wide Web 202 as part of Internet 200. Optionally, Web server system 216 may be part of an ISP which provides access to World Wide Web 102 client systems. Web server system 216 is shown coupled to server computer system 218 which itself may be coupled to relational database 240 and manufacture process 211. Relational database 240 may embody public and known expert knowledge.

It will be appreciated that while two computer systems 216 and 218 are shown in FIG. 3, Web server system 216 and server computer system 218 may be one computer system having different software components providing the Web server functionality and the server functionality provided by server computer system 218.

Although client computer systems 210, 212, and 214 may be in relationships of mutual benefit with or dependence upon World Wide Web 202 similar to client computer system 208, the connections are not the same for client computer systems 210, 212, and 214 as shown in FIG. 3. Client computer system 210 is coupled through modem interface 222 while client computer systems 212 and 214 are part of a Local Area Network (LAN) comprising network interfaces 224 and 226, LAN bus 228, and gateway computer system 230. Network interfaces 224 and 226 may be Ethernet network or other network interfaces. Client computer systems 212 and 214 are coupled to LAN bus 228 through network interfaces 224 and 226. To provide firewall and other Internet related services for the local area network, LAN bus 128 may be further coupled to gateway computer system 230. Gateway computer system 230, in turn, may be coupled to ISP 206 to provide Internet symbiosis to the client computer systems 212 and 214.

Client computer systems 208, 210, 212, and 214 may each view Web or HTML pages provided by the Web server system 216 when provided with the appropriate Web browsing software. These client computer systems may be a WINTEL® computer system, a network computer, a Web TV system, or other computer systems. Moreover, gateway computer system 230 may be, for example, a conventional server computer system. Also, Web server system 216 may be a conventional server computer system. And, although FIG. 3 shows interfaces 220 and 222 as modems, it will be appreciated that each of these interfaces may be an analog modem, Industry Standard Digital Network (ISDN) modem, cable modem, satellite transmission interface, for example, DIRECT PC®, or other interfaces for coupling a computer system to other computer systems.

In various exemplary embodiments, the server may comprise a predetermined base formula upon which the individual may "build" or add ingredients to in order to develop the proposed unique formula.

The base formula of various exemplary embodiments preferably comprises ingredients fundamental to many unique formulae. For example, the base formula may comprise of about 5 to about 20 percent carbohydrates. The base formula may comprise, for example, electrolytes.

The base formula of various exemplary embodiments is preferably at least substantially water soluble in various exemplary embodiments of the present invention.

It is preferred that the unique formula designed by the individual be at least substantially water soluble in various exemplary embodiments of the present invention.

In various exemplary embodiments, the approved unique formula produced for the individual is in the form of, for example, a powder, capsule, tablet, gel or liquid concentrate. In various exemplary embodiments, the approved unique formula produced for the individual is substantially homogeneous.

Various exemplary embodiments of the present invention further include a system for producing a unique digestible physical enhancer for an individual. The system of various exemplary embodiments comprises a client computer and a server computer or program.

The client computer of various exemplary embodiments displays one or more statements to the individual such that the one or more statements comprise potential formula ingredients. The client computer allows for an individual to interact with a server device, wherein the server device is a computer or program.

The server program of various exemplary embodiments receives one or more responses from the client computer indicating proposed formula ingredients chosen by the individual and amounts chosen by the individual, determines an absorption ability based upon the proposed formula ingredients chosen by the individual and amounts chosen by the individual, forwards proposed unique formula ingredients and amounts chosen by the individual to the individual, receives one or more modifications to the proposed unique formula ingredients and amounts from the individual if the individual makes any modifications, re-determines the absorption ability based upon the one more modifications made by the individual, receives approval of proposed unique formula from the individual, processes approved unique formula, and forwards processed approved unique formula to be produced for the individual.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

What is claimed is:

1. An interactive process for formulating a unique digestible physical enhancer for an individual by way of a computer system comprising:
    displaying one or more statements to the individual using a client's computer, wherein the statements comprise potential formula ingredients;
    receiving one or more responses at a server device from the client computer indicating proposed formula ingredients chosen by the individual and amounts of formula ingredients chosen by the individual;
    determining osmolality of the proposed formula ingredients to be equal to or less than a predetermined value;
    determining an absorption ability of proposed formula based upon proposed formula ingredients chosen by individual and amounts of formula ingredients chosen by the individual, wherein the absorption ability is determined based upon the osmolality;
    displaying the absorption ability as a calculated numeric value, as a numeric or relative value on a scale, or as a symbol or symbolic message, wherein the display indicates the absorption ability of the proposed formula is of an acceptable value or of a value greater than recommended;
    receiving approval of proposed unique formula by the individual;
    processing approved unique formula at the server device; and
    producing the approved unique formula for the individual.

2. The process according to claim 1, before the step of displaying one or more statements, further comprising:
    receiving one or more statements of the individual; and
    proposing one or more base formulae to the individual based on the one or more statements of the individual, wherein the statements of the individual relate to physical attributes of the individual and one or more intended physical activities of the individual.

3. The process according to claim 2, after proposing one or more base formulae, further comprising:
receiving one or more advanced statements of the individual; and
proposing one or more advanced base formulae to the individual based on the one or more advanced statements of the individual wherein the advanced statements of the individual relate to caloric needs, fluidic needs and electrolytic needs of the individual.

4. The process according to claim 1, further comprising displaying a determined absorption ability to the client computer after determining the absorption ability.

5. The process according to claim 1, further comprising displaying a determined absorption ability to the client computer when displaying the proposed unique formula ingredients and amounts of ingredients to the individual.

6. The process according to claim 1, wherein the ingredients chosen by the individual are added to a predetermined base formula.

7. The process according to claim 6, wherein the predetermined base formula comprises 5 to 20 percent carbohydrates.

8. The process according to claim 6, wherein the predetermined base formula comprises electrolytes.

9. The process according to claim 1, wherein the approved unique formula is substantially soluble in water.

10. The process according to claim 1, wherein the approved unique formula is a powder.

11. The process according to claim 1, wherein the approved unique formula is a gel.

12. The process according to claim 1, wherein the approved unique formula is a capsule or tablet.

13. The process according to claim 1, further comprising displaying recommended ingredients to the individual.

14. The process according to claim 13, wherein the recommended ingredients are based upon age of the individual.

15. The process according to claim 13, wherein the recommended ingredients are based upon the activity of the individual.

16. The process according to claim 13, wherein the recommended ingredients may be viewed by the individual at any point in the process.

17. An interactive process for formulating a unique digestible physical enhancer for an individual by way of a computer system comprising:
displaying one or more statements to the individual using a client's computer, wherein the statements comprise potential formula ingredients;
receiving one or more responses at a server device from the client computer indicating proposed formula ingredients chosen by the individual and amounts of formula ingredients chosen by the individual;
determining osmolality of the proposed formula ingredients to be equal to or less than a predetermined value;
determining an absorption ability of proposed formula based upon proposed formula ingredients chosen by individual and amounts of formula ingredients chosen by individual, wherein the absorption ability is determined based upon the osmolality;
displaying the absorption ability as a calculated numeric value, as a numeric or relative value on a scale, or as a symbol or symbolic message, wherein the display indicates the absorption ability of the proposed formula is of an acceptable value or of a value greater than recommended;
tailoring the enhancer by performing the following as many times as needed:
displaying proposed unique formula ingredients and amounts of ingredients to individual;
receiving one or more modifications from individual to proposed unique formula and amounts;
re-determining the osmolality of the proposed formula ingredients to be equal to or less than a predetermined value;
re-determining absorption ability based upon modifications made by individual to proposed unique formula ingredients and amounts of ingredients, wherein the absorption ability is determined based upon the osmolality;
re-displaying the absorption ability as a calculated numeric value, as a numeric or relative value on a scale, or as a symbol or symbolic message, wherein the display indicates the absorption ability of the proposed formula is of an acceptable value or of a value greater than recommended;
receiving approval of proposed unique formula by the individual;
processing approved unique formula at the server device; and
producing the approved unique formula for the individual.

18. The process according to claim 17, before the step of displaying one or more statements, further comprising:
receiving one or more statements of the individual; and
proposing one or more base formulae to the individual based on the one or more statements of the individual, wherein the statements of the individual relate to physical attributes of the individual and one or more intended physical activities of the individual.

19. The process according to claim 18, after proposing one or more base formulae, further comprising:
receiving one or more advanced statements of the individual; and
proposing one or more advanced base formulae to the individual based on the one or more advanced statements of the individual wherein the advanced statements of the individual relate to caloric needs, fluidic needs and electrolytic needs of the individual.

20. The process according to claim 17, further comprising displaying a determined absorption ability to the client computer after determining the absorption ability.

21. A system for formulating a unique digestible physical enhancer for an individual comprising:
a client computer, wherein the client computer displays one or more statements to the individual such that the one or more statements comprise potential formula ingredients;
a server device, wherein the server device
receives one or more responses from the client computer indicating proposed formula ingredients chosen by the individual and amounts chosen by the individual,
determines osmolality of the proposed formula ingredients to be equal to or less than a predetermined value;
determines an absorption ability based upon the proposed formula ingredients chosen by the individual and amounts chosen by the individual, wherein the absorption ability is determined based upon the osmolality,
displays the absorption ability as a calculated numeric value, as a numeric or relative value on a scale, or as a symbol or symbolic message, wherein the display indicates the absorption ability of the proposed formula is of an acceptable value or of a value greater than recommended:

forwards proposed unique formula ingredients and amounts chosen by the individual to the individual, receives one or more modifications to the proposed unique formula ingredients and amounts from the individual, re-determines the absorption ability based upon the one more modifications made by the individual, receives approval of proposed unique formula from the individual, processes approved unique formula, and forwards processed approved unique formula to be produced for the individual.

\* \* \* \* \*